US009848781B2

(12) United States Patent
Suesstrunk et al.

(10) Patent No.: US 9,848,781 B2
(45) Date of Patent: Dec. 26, 2017

(54) EQUIPMENT AND METHOD FOR CONTINUALLY MEASURING THE BLOOD PRESSURE FOR MONITORING PURPOSES

(75) Inventors: Heinz Suesstrunk, Langnau (CH); Etienne Hirt, Zurich (CH)

(73) Assignee: STBL Medical Research AG, Wilen (CH)

( * ) Notice: Subject to any disclaimer, the term of this patent is extended or adjusted under 35 U.S.C. 154(b) by 605 days.

(21) Appl. No.: 13/058,501

(22) PCT Filed: Aug. 12, 2009

(86) PCT No.: PCT/EP2009/005850
§ 371 (c)(1),
(2), (4) Date: Mar. 14, 2011

(87) PCT Pub. No.: WO2010/017973
PCT Pub. Date: Feb. 18, 2010

(65) Prior Publication Data
US 2011/0166461 A1 Jul. 7, 2011

(30) Foreign Application Priority Data
Aug. 15, 2008 (CH) ...................................... 1295/08

(51) Int. Cl.
*A61B 5/0225* (2006.01)
*A61B 5/021* (2006.01)
(Continued)

(52) U.S. Cl.
CPC .......... *A61B 5/021* (2013.01); *A61B 5/02225* (2013.01); *A61B 5/02416* (2013.01);
(Continued)

(58) Field of Classification Search
CPC ...... A61B 5/021; A61B 5/02438; A61B 5/681
(Continued)

(56) References Cited

U.S. PATENT DOCUMENTS 4,331,154 A * 5/1982 Broadwater et al. ......... 600/490
4,409,983 A * 10/1983 Albert .......................... 600/503
(Continued)

FOREIGN PATENT DOCUMENTS

DE 10 2005 059435 A1 6/2007
WO WO 97/03606 A 2/1997
(Continued)

OTHER PUBLICATIONS

International Search Report of corresponding international Application No. PCT/EP2009/005850, dated Oct. 30, 2009.
(Continued)

*Primary Examiner* — Christian Jang
*Assistant Examiner* — Michael Catina
(74) *Attorney, Agent, or Firm* — Alston & Bird LLP

(57) ABSTRACT

The equipment has at least one pressure sensor (28) disposed for being placed onto the surface of the body of the user and being held attached thereto by means of a band. The attachment force is selected such that the pressure signal from the pressure sensor (28) contains variations caused by the pulse. An attachment pressure sensor (52) or a band tension sensor (18') generates an electrical signal depending on the attachment pressure. The microprocessor (36) determines the diastolic and systolic blood pressure values from the pressure signal, taking into account the signal from the attachment pressure sensor (52) or the band tension sensor (18').

19 Claims, 12 Drawing Sheets

(51) Int. Cl.
*A61B 5/022* (2006.01)
*A61B 5/024* (2006.01)
*A61B 5/00* (2006.01)
*A61B 5/11* (2006.01)

(52) U.S. Cl.
CPC ............ *A61B 5/681* (2013.01); *A61B 5/0002* (2013.01); *A61B 5/11* (2013.01); *A61B 5/721* (2013.01)

(58) Field of Classification Search
USPC ........................................................ 600/503
See application file for complete search history.

(56) References Cited

U.S. PATENT DOCUMENTS

| | | | |
|---|---|---|---|
| 5,494,043 A | 2/1996 | O'Sullivan et al. | |
| 6,245,024 B1* | 6/2001 | Montagnino et al. | 600/499 |
| 6,443,906 B1* | 9/2002 | Ting | A61B 5/022 600/485 |
| 6,533,729 B1* | 3/2003 | Khair et al. | 600/503 |
| 2001/0020134 A1* | 9/2001 | Nissila | A61B 5/02438 600/503 |
| 2003/0208127 A1* | 11/2003 | Archibald et al. | 600/494 |
| 2004/0199081 A1* | 10/2004 | Freund et al. | 600/485 |
| 2005/0228296 A1 | 10/2005 | Banet | |
| 2007/0088220 A1* | 4/2007 | Stahmann | 600/485 |
| 2008/0262535 A1* | 10/2008 | Gavriely et al. | 606/203 |

FOREIGN PATENT DOCUMENTS

| | | |
|---|---|---|
| WO | WO 99/08591 A | 2/1999 |
| WO | WO 01/85024 A | 11/2001 |
| WO | WO 02/30277 A2 | 4/2002 |
| WO | WO 2004/004558 A | 1/2004 |

OTHER PUBLICATIONS

International Preliminary Report on Patentability of corresponding international Application No. PCT/EP2009/005850, dated Feb. 15, 2011 (English Translation).
International Preliminary Report on Patentability of corresponding international Application No. PCT/EP2009/005850, dated Feb. 15, 2011.
Shaltis, et al., Calibration of the Photoplethysmogram to Arterial Blood Pressure: Capabilities and Limitations for Continuous Pressure Monitoring, *Proceedings of the 2005 IEEE, Engineering in Medicine and Biology 27th Annual Conference*, Sep. 1-4, 2005, pp. 3970-3973.
European Patent Office, Notification in Accordance with Article 94(3) of the EPC for Application No. 09777834.4, dated Jun. 13, 2013, 8 pages, Germany.

\* cited by examiner

| Time (s) | Accel. X-axis (a) | Accel. Y-axis (a) | Accel. Z-axis (a) | Skin temp. (°C) | Ref. temp. (V) | Temp. pressure sensor 1 (V) | Pressure sensor 1 (V) | Pressure sensor 2 (V) | Pressure sensor 3 (V) | Pressure sensor 4 (V) | Ref. sensor (V) |
|---|---|---|---|---|---|---|---|---|---|---|---|
| 0.000 | 0.21 | 1.01 | 0.03 | 31.9 | 2.134 | 2.134 | 0.30471 | 0.31964 | 0.33318 | 0.38081 | 0.25496 |
| 0.017 | 0.21 | 0.98 | 0.06 | 31.9 | 2.134 | 2.134 | 0.30485 | 0.31981 | 0.33327 | 0.38062 | 0.25491 |
| 0.033 | 0.2 | 1 | 0.06 | 31.9 | 2.134 | 2.135 | 0.30473 | 0.31982 | 0.33327 | 0.38097 | 0.25499 |
| 0.050 | 0.21 | 0.99 | 0.03 | 31.9 | 2.134 | 2.134 | 0.30483 | 0.31995 | 0.33327 | 0.38064 | 0.25493 |
| 0.067 | 0.21 | 0.99 | 0.04 | 32 | 2.134 | 2.135 | 0.30496 | 0.31981 | 0.33319 | 0.38057 | 0.25496 |

FIG. 3

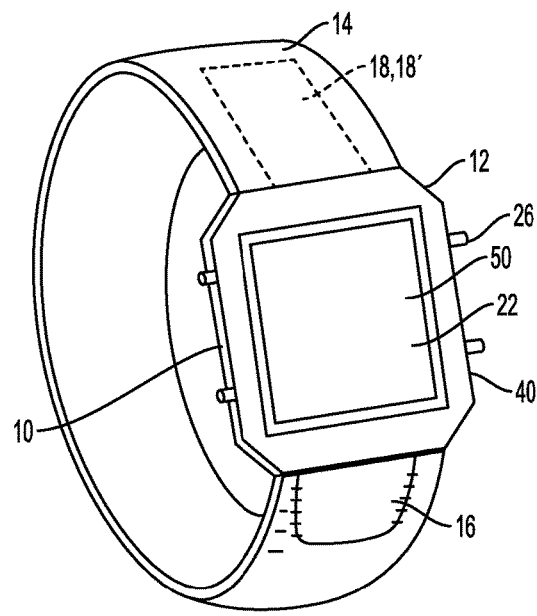
FIG. 8
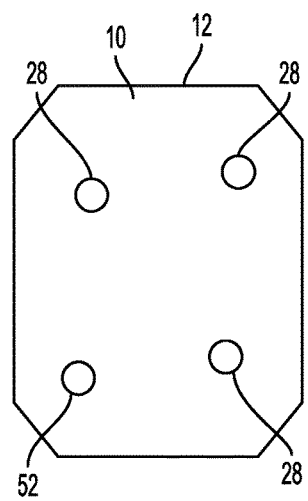 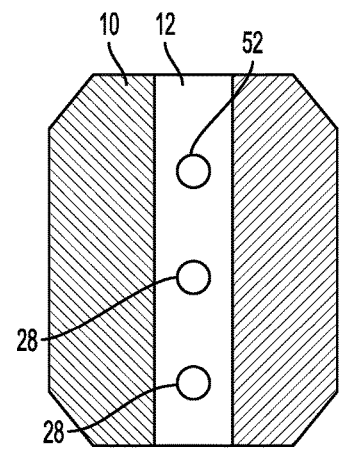
FIG. 9  FIG. 10

EQUIPMENT AND METHOD FOR CONTINUALLY MEASURING THE BLOOD PRESSURE FOR MONITORING PURPOSES

CROSS REFERENCE TO RELATED APPLICATIONS

This application is a national stage application, filed under 35 U.S.C. §371, of International Application No. PCT/EP2009/005850, filed Aug. 12, 2009, which claims priority to Switzerland Application No. CH 2008 01295/08, filed Aug. 15, 2008, both of which are hereby incorporated by reference in their entirety.

BACKGROUND OF THE INVENTION

Field of Invention

The present invention relates to an apparatus and a method for continuously measuring the blood pressure for monitoring purposes, as per claims 1 and 13. The apparatus and the method are particularly suitable for the long-term measurement of the blood pressure in a healthy and an ill body, and so a dangerously raised or lowered blood pressure can be identified at an early stage.

When the heart beats, a pressure wave is generated with every beat or each cardiac contraction and it propagates through the entire body from the heart. For the most part, the body consists of water and so this propagation takes place not only in the arteries but extends to all blood vessels and, in end effect, to the entire body tissue. The artery is expanded elastically with each heart beat, and it subsequently contracts. In the process, the column of blood is advanced from the heart, and a return flow is prevented by closing the cardiac valves. The blood pressure peaks when the heart contracts (duration: approximately 0.15 seconds) and presses the blood into the arteries, which are expanded as a result of this. The maximum pressure generated thereby is called the systolic blood pressure. The blood pressure is at its lowest when the heart relaxes again (duration: 0.7 seconds) and the vessels once again obtain their normal state. The pressure occurring here is called the diastolic blood pressure. The systolic blood pressure is always stated first, followed by the diastolic blood pressure. 140/80 (pronounced "one-forty over eighty") thus means that the systolic blood pressure has a value of 140 and the diastolic blood pressure has a value of 80. However, the blood pressure is not always constant but varies over the course of a day. Influencing variables include, for example, the time of day, stress, physical exertion, smoking, resting and relaxation.

Description of Related Art

The most common methods of non-invasive blood-pressure measurement are the sphygmomanometric and the plethysmographic measurement methods. Both provide measurements of the blood pressure with the aid of pressure cuffs as per the principle of Riva-Rocci. These are indirect measurement methods, in which the extremal values of the pressure range in the arterial system are measured. They only permit occasional measurements and do not allow continuous collection of the pressure conditions. The auscultatory measurement using a mercury column (sphygmomanometer) is considered to be the historically evolved "gold standard" of indirect blood-pressure measurement (Riva-Rocci method). The other measurement methods are usually compared to this standard. Current therapy methods are generally based on the auscultatory measurement.

The oscillometric method has been known since the beginning of the twentieth century. Almost all commercially available semi-automatic and automatic apparatus measure in an oscillometric fashion. This measurement method is based on the pressure variations of the pulse wave (oscillation). This oscillation is registered by the pressure transducer in the apparatus and converted into blood-pressure values.

Currently available apparatus for blood-pressure measurement on the wrist operate according to the oscillometric measurement principle. However, these apparatus are rather unsuitable for use in a surgery or in hospital. Initial comparison measurements have to be carried out on the upper arm. All automatic or semi-automatic blood-pressure measuring apparatus in Europe must be validated according to a European norm. Since 1995, this CE certification (European norm) provides for non-invasive blood-pressure measuring apparatus to be allowed to bear the CE mark if they have been validated according to the European norm EN-1060 for non-invasive blood-pressure measuring apparatus. The goal of the CE certification lies in the harmonization of apparatus quality within the European Union. Five areas of examination are covered in the CE certification for electronic blood-pressure apparatus. CE certification demands that at least 85 persons are included in the examination procedure relating to the measurement accuracy. The mean deviation, as a measure for the systematic deviation, from an auscultatory measurement on the upper arm may be no more than 5 mmHg (the standard deviation may be no more than 8 mmHg). The comparison measurements are carried out in parallel on the same arm, sequentially, or in parallel on the other arm. The CE certification guarantees proper function in terms of technology and equipment. However, the comparison measurements should not be carried out on patients with high or low blood pressure. Thus this validation does not allow much to be said in relation to the measurement accuracy in clinical day-to-day use. The British Hypertension Society (BHS) protocol for validating automatic and semi-automatic blood-pressure measuring apparatus was introduced in 1990. This protocol currently is the most refined method allowing a differentiated assessment of the measurement accuracy. The assessment within the BHS validation consists of the grading A, B, C and D in accordance with the table below, which points out the difference between the standard sphygmomanometer and the test equipment (mmHg):

| Grading | <5 mmHg | <10 mmHg | <15 mmHg |
|---------|---------|----------|----------|
| A | 80% | 90% | 95% |
| B | 65% | 85% | 95% |
| C | 45% | 75% | 90% |
| D | Grading C not satisfied | | |

The specifications in percent relate to the measurements within the respectively specified difference. A "B" grading means that 85% of the measurements yield values that deviate by less than 10 mmHg from the auscultatory upper arm measurement. A blood-pressure measuring apparatus should have at least an overall grading of B/B (systolic/diastolic blood pressure).

Only clinically validated apparatus should be utilized in professional use. With the exception of pulse-wave velocity measurement, previous apparatus and methods are usually based on the cuff principle and thus only allow an occasional measurement (instantaneous reading) and not a continuous collection of the pressure conditions.

The document EP 1 341 436 has disclosed a device for continuous monitoring of the arterial blood pressure. The sensor means thereof should be positioned on the external surface of the user body at a site adjacent to an artery and a protruding section of the sensor means should be pressed so firmly against the surface by means of a belt or a band that there is at least a partial occlusion of the artery. This impedes the blood flow in the artery.

BRIEF SUMMARY OF THE INVENTION

It is an object of the present invention to develop an apparatus and a method for measuring the blood pressure, in the human body in particular, continuously for monitoring purposes, without the use of pressure cuffs.

Herein, the apparatus should be compact, similar to a wristwatch and able to be worn during almost all physical activities with the exception of during e.g. swimming or bathing if need be.

This object is achieved by an apparatus with the features of claim 1 and by a method as per claim 13.

According to the invention, the pressure is measured at a suitable site of the preferably human body by means of a pressure sensor. A band (this term for example also comprises a band made of or with chain links) holds the pressure sensor at the location with safe, functional contact; the contact should be so close that the pressure sensor remains at the location even when the body moves, but does not occlude or partly occlude an artery. Hence the pressure sensor measures the bearing pressure superposed by a pressure variation caused by the blood pressure.

Suitable locations are more particularly found on the extremities, for example on the forearm, upper arm or lower leg. The location need not be situated above an artery, but this is possible.

In order to be able to compensate for the bearing pressure when processing the pressure signal generated by the pressure sensor, provision is made for either a contact-pressure sensor, which is preferably placed in the vicinity of the pressure sensor, or a band-tension sensor.

The contact-pressure sensor is also held with contact against the external surface of the body by means of the band; however, this is preferably brought about with less pressure than the pressure sensor, and so the contact-pressure sensor measures the pressure with which it rests against the surface, but with at least almost no superposition of a pressure variation superposed by the blood pressure.

The band-tension sensor, which is present as an alternative to the contact-pressure sensor or in addition thereto, measures the tensile stress of the band. It goes without saying that both the band-tension sensor and the contact-pressure sensor generate an appropriate output signal that represents a measure of the bearing pressure of the pressure sensor.

Various circumstances can lead to a change in the girth of the body at the measurement site, for example in the girth of the relevant extremity. By way of example, the girth changes if the muscles are tensed, during physical exercise, etc. This change in the girth leads to a change in the bearing pressure of the pressure sensor; this can be taken into account when processing the pressure signal by means of the contact-pressure sensor or band-tension sensor.

Preferred embodiments of the invention are specified in the dependent claims.

BRIEF DESCRIPTION OF THE FIGURES

The invention will be explained in more detail on the basis of the embodiments illustrated in the drawing, in which, in a purely schematic fashion:

FIG. 3 shows measurement results from four pressure sensors in millivolt in a table, as well as the values from an accelerometer and the temperature values of the skin;

FIG. 8 shows a perspective illustration of a further embodiment of the apparatus according to the invention with a band-tension sensor integrated into an armband;

FIG. 9 shows a view of the base of the housing of the apparatus with a possible arrangement of four sensors;

FIG. 10 shows a view of the base of the housing of the apparatus with a possible further arrangement of three sensors;

DETAILED DESCRIPTION OF VARIOUS EMBODIMENTS OF THE INVENTION

Figure 1:
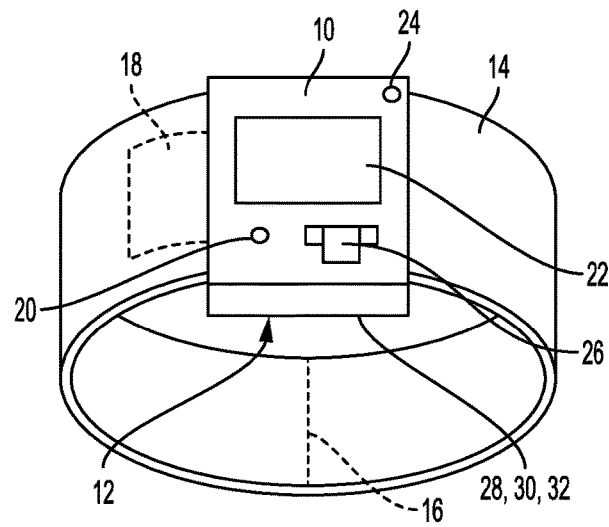
FIG. 1 shows a perspective schematic illustration of an apparatus for continuously measuring the blood pressure for monitoring purposes.

The pulse, or the pressure wave generated thereby, transports red blood cells and a few small platelets through the body. The blood of an adult human contains approximately 5 million red blood cells and approximately 6000 white blood cells. The number of red blood cells in particular is linearly related to the blood volume. However, the density of red blood cells influences the absorption of infrared beams, which penetrate approximately 1 mm into the skin, and so the absorption or reflection of infrared radiation penetrating the skin can be measured by an infrared transmitter/detector. Yet this allows the detection of the pulse by registering the infrared absorption or reflection. Hence the pulse curve can be illustrated as a curve in the form of a succession of electrical signals. This results in a sinusoidal shape of the curve. This fact is also used for establishing the blood pressure in accordance with the method. Secondly, the measurement method assumes the fact that the body mainly consists of incompressible water; that is to say its interior forms an aqueous solution. Hence a pressure wave propagates virtually without damping through the body tissue. Here the transmural pressure defines is a partial pressure, and which corresponds to the blood pressure.

A further parameter that can be taken into account, if need be, is the air pressure acting on the body from the outside. Finally, a measurement can also be influenced by the acceleration of the measurement location, which acceleration, optionally, may therefore also be registered in order to be compensated for in the measurement result.

The apparatus and the method for continuously measuring the blood pressure are based on measuring the interpretation of the aforementioned values. This should firstly be explained with reference to an exemplary trial arrangement. Four pressure sensors on a bearing plate were brought to bear with contact on the surface of the skin, more precisely on the forearm in the vicinity of the wrist, opposite to the location where a wristwatch is worn and where the pulse is generally felt. Reference is made here to the fact that further trials have shown that the pressure sensors or the pressure sensor can also be attached to other suitable locations, for example where a wristwatch is usually worn, on the upper arm or on the leg, etc.

The aforementioned pressure sensors were used to measure the pressure on the skin surface, which pressure contains the transmural pressure as a partial pressure. The pulse was determined separately therefrom at this measurement location by emitting infrared radiation into the tissue by means of an infrared transmitter and detecting the reflection. It was possible to show that the pressure waves of the pulse correlated to the pressure values measured by the four pressure sensors. This always afforded the possibility of localizing where the diastolic pressure and where the systolic pressure was imaged on the pressure-value curve by means of the pulse curve. However, this image only permitted a qualitative interpretation. The blood pressure still was a superposed value contained in the measured pressure values. In order to check the absolute values, it goes without saying that the blood pressure could not be measured on the same arm of the subject in a conventional fashion as per Riva-Rocci by using a pressure cuff on the left upper arm. Rather the measured data was compared to that from an oscillometric measurement method.

FIG. 1 illustrates an apparatus that can be worn like a wristwatch. A bearing plate 10, which in this case forms a housing 12, is integrated into an armband 14, which is equipped with a catch 16 (not illustrated in any more detail), and the bearing plate 10, when worn, for example comes to rest on the location of the forearm that is opposite to the place where a wristwatch is normally worn and where the pulse is usually measured; however, as explained above, other locations are also possible.

The bearing plate 10 should rest evenly on this location of the forearm with contact pressure that stays as constant as possible. The armband 14 is equipped with a strain sensor 18 that registers a measure of the band tension. If the armband 14 is stretched as a result of a swelling of the arm brought about by a change in temperature or by physical activity, this is registered by the strain sensor 18 and can be compensated for in the measurement. There is a pressure sensor 20 (air-pressure sensor) for establishing the current atmospheric pressure on the upper side of or laterally on the bearing plate. On the upper side of the bearing plate 10, the latter has a display 22 for displaying the measured diastolic and systolic blood pressure, and an optical alarm lamp 24. Moreover, the input keys 26 are assigned.

A plurality of pressure sensors 28 are arranged on the underside of the bearing plate 10, and are thus not visible here, and so the sensitive side thereof is directed downward, i.e. against the skin of the wearer. An infrared sensor 30, with an associated detector 32, is likewise integrated on the underside, and so infrared light can be emitted into the skin of the wearer and the reflection can be detected. An integrated circuit is housed in the interior of the bearing plate 10, and said circuit is explained in more detail below.

Figure 2:
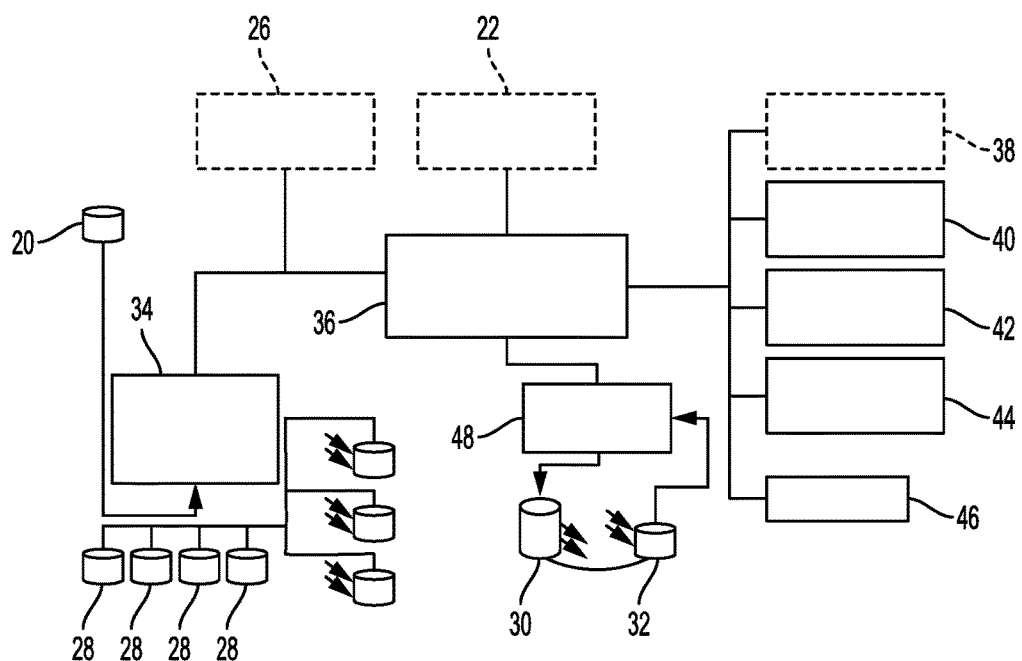
FIG. 2 shows a first diagram of the measurement arrangement and the electronic circuit thereof.

FIG. 2 shows a diagram of the measurement arrangement and this electronic circuit. The four pressure sensors 28 with a sensitivity between 0 and 1.5 bars can be seen bottom left. By way of example, they each contain one piezocrystal, and so a voltage that is linear with respect to the pressure value is emitted in the case of a pressure load. A further pressure sensor (the air-pressure sensor 20) measures the currently prevalent atmospheric pressure. The signals by these pressure sensors 28 and the air-pressure sensor 20 emitted in the form of voltages are then transmitted to an A/D converter 34 and, from there, on to a microprocessor 36. The microprocessor 36 can be operated by means of the input keys 26, and the output values of said microprocessor can be displayed on a display 22. The microprocessor 36 is furthermore connected to an RF interface 38, and to a USB interface 40, for reading out the data on an external computer. The microprocessor 36 moreover is connected to a storage device 42, and also to a current supply 44 (battery and mains connection). An accelerometer 46 is also connected; the electrical signals thereof are fed to the microprocessor 36. The infrared transmitter 30 and the associated infrared detector 32 for measuring the pulses are illustrated below the microprocessor 36. 48 is used to denote an amplifier for actuating the infrared transmitter 30 and a D/A converter.

The blood pressure of 15 patients, namely 5 women and 10 men with an age of between 27 and 59 years, was measured by means of the present apparatus and the present method, that is to say by the four pressure sensors 28 as shown in FIG. 1, and these were placed at a distance of 5 cm from the left wrist or applied by means of the bearing plate 10, opposite to the location where the wristwatch is worn, and the obtained values were compared to the values from a simultaneously undertaken oscillometric measurement on the right upper arm, undertaken using an Acutron Mindray SV 800 apparatus. The measurements were carried out in a relaxed seated position, once in a completely relaxed, rested state of the subject, and once after light physical exertion. The individual measurements were respectively carried out over 30 seconds, to be precise once in a relaxed seated position, once with a closed nose and mouth and with pressing respiratory air therein (Valsalva maneuver), once with simultaneous drumming of fingers, and once with isometric tensing of the forearm muscles, and finally once with a continuous pump motion with the fingers (clenching the fist and releasing after 30 seconds). The measurement results from the pressure sensors 28 (the pressure signals) were firstly available in millivolt. Since no cuffs were used, this means that the undertaken comparison is not compatible with the requirements of either the British Hypertension Society BHS or the American Association for the Improvement of Scientific Apparatus AASI.

FIG. 3 shows the measurement results of the four pressure sensors 28 in millivolt with the aid of a table, which results are registered over a period of 67 seconds. This table also contains the values of the additional accelerometer 46, as well as the measured skin temperature and a reference value for the sensor temperature. The last column specifies the pressure value from the additional air-pressure sensor 20. In total, 225 measurements were undertaken using both methods, i.e. the conventional oscillometric method and the novel, pressure-sensor-based method, and compared. 108 of these comparisons were investigated in more detail. It is obvious that additional measurements are required, using persons of different sex, age, size, weight, initial blood-pressure values, arm lengths, etc.

Figure 4:
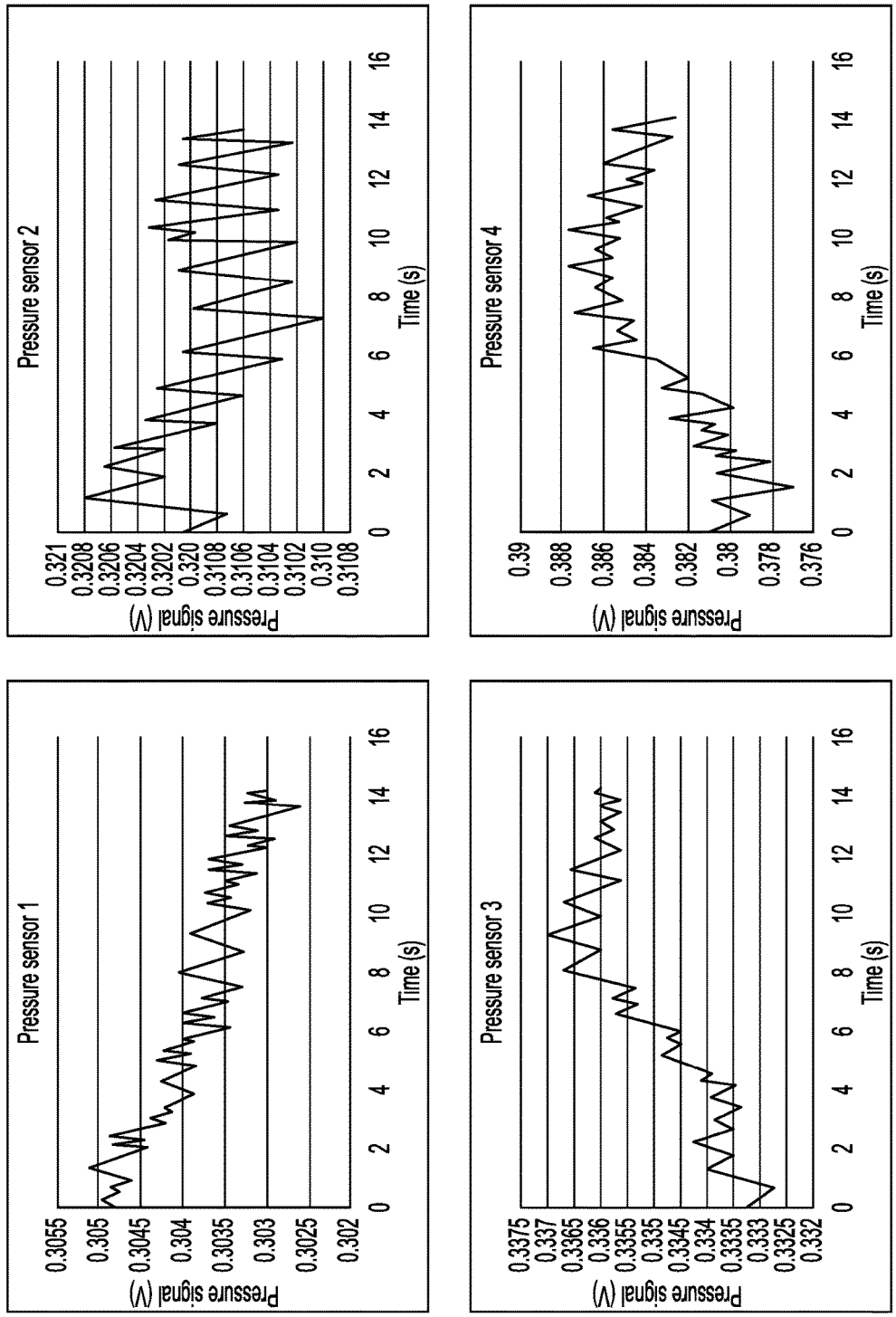
FIG. 4 shows the measurement results from the four pressure sensors in millivolt, plotted over time.

FIG. 4 shows the measurement results of the four pressure sensors in millivolt, plotted over time. This shows that each value faithfully oscillates between local maxima and minima, between approximately 0.319 mV and approximately 0.388 mV, and that the peaks of the four graphs mutually correlate in time. From these four blood-pressure curves, the curve with the second-lowest absolute values (pressure sensor 2) around the diastolic blood pressure and the associated higher systolic values was selected, as well as the curve with the highest absolute values around the diastolic blood pressure (pressure sensor 4) and the associated higher systolic blood pressure. The values can be averaged, and a fluctuation curve is obtained for the pressure value containing the transmural pressure.

Figure 5:
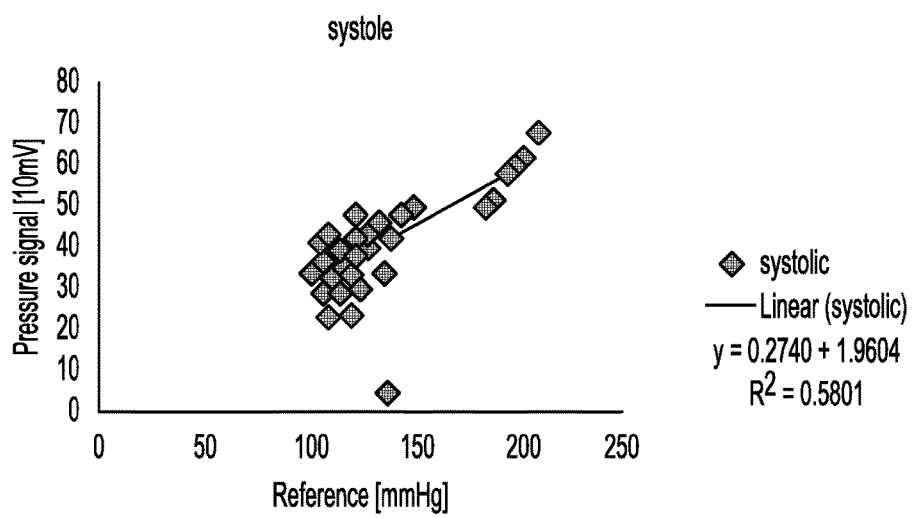
FIG. 5 shows a graph of the measurement values for the systolic pressure, correlated with the results of an oscillometric measurement of the blood pressure.
Figure 6:
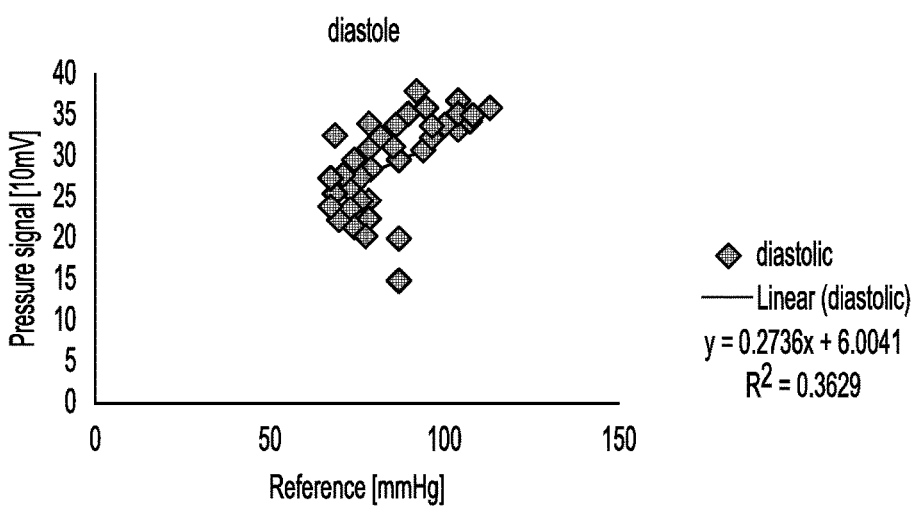
FIG. 6 shows a graph of the measurement values for the diastolic pressure, correlated with the results of an oscillometric measurement of the blood pressure.

The blood-pressure values measured in an oscillometric fashion and the pressure-sensor values in millivolt were compared for each 30-second period and correlated to one another. FIG. 5 shows a graph of how these averaged measurement values for the systolic pressure correlate with the results of an oscillometric measurement of the blood pressure between 97 and 214 mmHg. And FIG. 6 shows the correlation for the diastolic blood pressure between 96 and 107 mmHg. Thus, a linear function could be established for both the lower, diastolic blood-pressure value and for the upper, systolic blood-pressure value. In the process, the expected differences could be detected in relation to the measurements of the basic tension caused by relaxed and tensed muscles.

Figure 7:
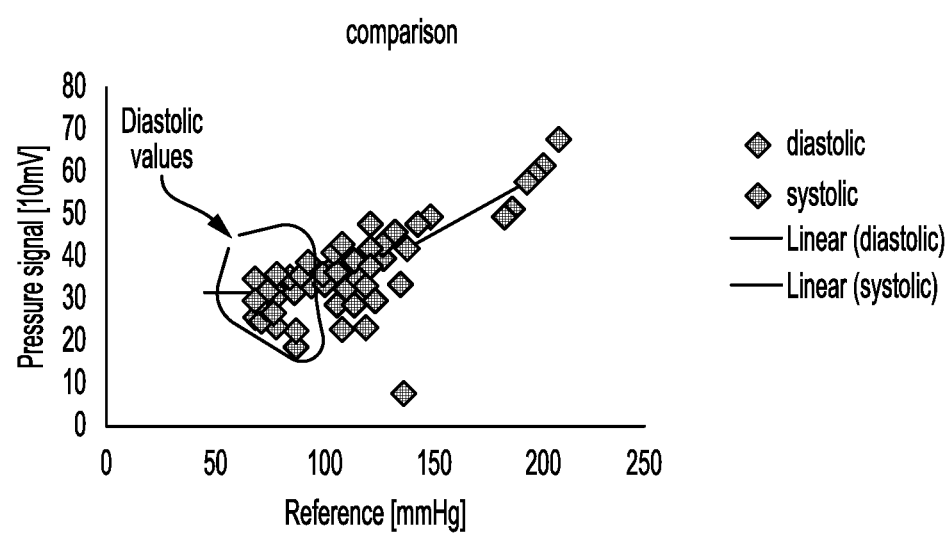
FIG. 7 shows a graph of a comparison of the measurement values for the systolic pressure and the diastolic pressure, correlated with the results of an oscillometric measurement of the blood pressure.

The same also applies for the comparison of the two blood-pressure values as shown in FIG. 7. Here the measurement values for the systolic pressure and the diastolic pressure are graphed, correlated to the results of an oscillometric measurement of the blood pressure. Three different clusters of measurement points can be identified: one in the region of an increased blood pressure around the region up to 214 mmHg; a second cluster of measurement points lies in the region of approximately 145 mmHg and a third around 60 to 120 mmHg. The linearity between the values obtained by the pressure sensors 28 and those obtained from the oscillometric values remains unchanged, and the fluctuations in the measurement values are situated within a narrow band.

The relationship between the oscillometric method used as reference and the pressure-sensor-based method appears to be very precise, with a clear linearity in the relationship. The pressure-sensor-based method is promising, at least for measurements of the relaxing or only slightly physically active subject.

It is remarkable that no qualitative difference was determined in the comparison between the systolic and the diastolic blood pressure. Establishing the diastolic blood pressure, which generally is more difficult to measure, is therefore found to be no more demanding using this pressure-sensor method than measuring the systolic blood pressure. The pulse and also the blood-pressure curve with its typical rise and the so-called c-wave in the fall are clearly identifiable. This can also allow conclusions to be drawn about the state of the blood vessels. While conventional oscillometric apparatus require a 30-second period for measuring the blood pressure, this pressure-sensor apparatus and method allow a measurement from heartbeat to heartbeat, i.e. a continuous measurement and hence monitoring around the clock. As soon as certain adjustable values are exceeded, an acoustic or optical signal can be triggered on the apparatus, or an external automatic alarm can be triggered via the interfaces.

Taking into account the values from the accelerometer also allows the compensation of the measurement values for a moving subject, i.e. if, for example, the subject is walking and swinging their arms or if they are seated and swinging their arms or if they are seated and moving their arms, for example within the scope of normal office activity. It is understood that the measured voltage values have to be checked regularly and have to be adjusted in each individual case on the wearer of such an apparatus. However, wearing an apparatus operating on this basis allows continuous measurement of the blood pressure to the extent that an unexpected deflection, upward in particular, but downward as well, can now be detected.

FIG. 8 shows a further embodiment of the apparatus according to the invention with the housing 12 and the armband 14 inspired by a wristwatch. The housing 12 has the bearing plate 10 on its underside and a cover glass on its upper side, with the display 22 situated therebelow. Four input keys 26 are arranged on the lateral side of the housing 12. Furthermore, the USB interface 40 plug is located on the lateral side.

In the armband 14 there is a band-tension sensor 18' in the form of the strain sensor 18. The catch 16 affords the possibility of affixing the apparatus on the suitable location of the extremity so that it is fixed at its location. The catch 16 is preferably embodied as a stepped catch so that the tension, by means of which the armband 14, or more generally the band, can be tightened to a greater extent in a stepped fashion and tightened to a lesser extent in a stepped fashion.

The remaining elements arranged in or on the housing 12 are mentioned further below in conjunction with the description of FIGS. 9-16.

FIG. 9 shows the housing 12 as viewed from below, and thus the underside of the bearing plate 10 forming the base of the housing 12. Three pressure sensors 28 and a contact-pressure sensor 52 are associated with this bearing plate 10. This contact-pressure sensor 52 may be present instead of the band-tension sensor 18'. However, if there is a band-tension sensor 18', provision can be made for a fourth pressure sensor 28 in place of the contact-pressure sensor 52.

In the exemplary embodiment shown in FIG. 9, the three pressure sensors 18 and the contact-pressure sensor 52 are arranged approximately in the corners of a rhombus and are spaced from the edge of the bearing plate 10.

FIG. 10 shows, in an illustration like that of FIG. 9, a linear arrangement of two pressure sensors 28 and the contact-pressure sensor 52 or three pressure sensors 28 should a band-tension sensor 18' be available. The three sensors are situated in a row along a straight line, which extends along the longitudinal direction of the armband 14 and is in the center of the bearing plate 10.

Figure 11:
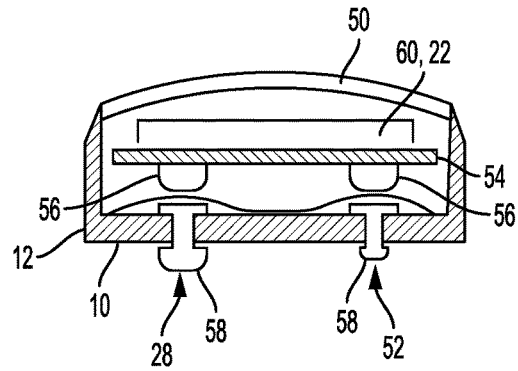
FIG. 11 shows a longitudinal section through the housing with, inter alia, a pressure sensor and a contact-pressure sensor.

It can be gathered from FIG. 11 that in the exemplary embodiment shown the difference between the pressure sensors 28 and the contact-pressure sensor 52 consists of the fact that latter protrudes less over the free surface of the bearing plate 10 than the pressure sensors 28, preferably by about half the amount.

Trials have shown that pressure sensors 28 protruding between approximately 0.5 mm and approximately 1 mm over the bearing plate 10 result in good measurement results and allow comfortable wearing of the apparatus.

In the interior of the housing 12 there is a printed circuit board 54, with the electronic circuit and the piezoresistive sensor elements 56 of the pressure sensors 28 and the contact-pressure sensor 52 being arranged thereon. Additionally, the pressure sensors 28 and the contact-pressure sensor 52 have plungers 58, which penetrate through the bearing plate 10 at right angles without being impeded and interact with the associated sensor element 56 with their end face arranged within the housing 12. A sealing membrane may be present between the sensor elements 56 and the plungers 58 for sealing purposes in order to prevent the ingress of dirt particles or water to the electronic circuit. The plungers 58 preferably have a button-head-like design on their external free ends in order to prevent pressure sites and injury to the user of the apparatus.

It goes without saying that in this respect many different solutions are feasible.

Figure 12:
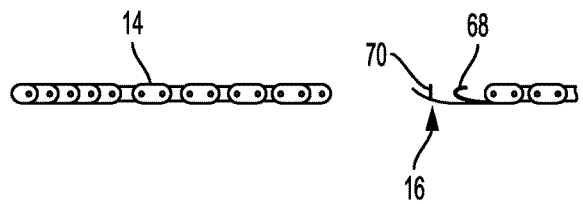
FIG. 12 shows a side view of a band, embodied as a chain, with a catch.
Figure 13:
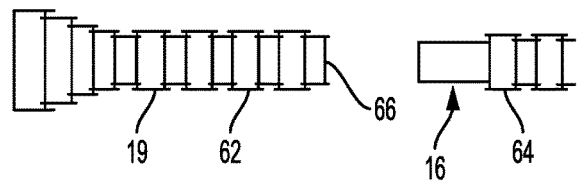
FIG. 13 shows a top view of the chain with catch as per FIG. 12.

FIGS. 12 and 13 show an embodiment of the band 14 designed as a chain. It has two sections 62, 64, each embodied as an articulated chain, for example as Gall's articulated chain. The section 62 is hinged to the housing 12 on one end and is intended to interact with a hook 68 and a securing tab 70 of the catch 16 by means of its bolts 66 on its end region distant from the housing. This flap-like catch 16, known per se from the watch-making industry, is attached to the last hook 68 of the section 64 in a pivotable fashion. The end of the section 64 distant to the catch 16 is hinged to either the housing 12 or a band-tension sensor 18', as will be described in conjunction with FIGS. 14 and 15.

The embodiment of the band 14 shown in FIGS. 12 and 13 allows the band 14 to be tightened in concrete steps, and to be released, in the style of a stepped catch. Instead of the illustrated embodiment of the catch 16 as a stepped catch, a catch as known from ski boots or from the watch-making industry is also feasible.

The section 62, or the corresponding section of the band 14, is hinged to attachment ears 72 of the housing 12 in a known fashion. So as to be able to measure the tension acting on the band 14 in the case of a practically inelastic embodiment of the band 14 in particular, the section 64, or the corresponding section of the band 14, can be hinged to a band-tension sensor 18', as illustrated in FIGS. 14 and 15.

These embodiments of the band-tension sensor 18' have a C-shaped or U-shaped frame 74. The two mutually parallel legs 76 of the frame 74 form attachment ears for hinging on the section 64 of the chain or the corresponding section of the band 14. The two legs 76 are guided through the lateral wall 78 of the housing 12 such that they can move freely in their longitudinal direction and are fixedly interconnected in the interior of the housing 12 via a web 80. A compression spring 82 acts between the web 80 and the lateral wall 78.

Figures 14, 15:
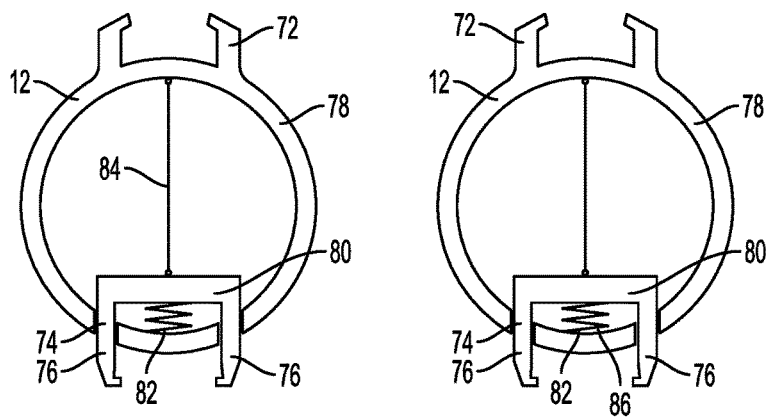
FIG. 14 shows a section through the housing with a band-tension sensor.
FIG. 15 shows an embodiment with a different band-tension sensor, illustrated as in FIG. 14.

In the embodiment shown in FIG. 14, a displacement transducer 84 acts between the web 80 and the lateral wall 78. Said transducer generates (as a function of the compression of the compression spring 82) an electrical band-tension signal as a function of the tension with which the band 14 or the chain is pulled.

In the embodiment shown in FIG. 15, a strain gauge 86 is arranged on the compression spring 82 itself in order to generate an electrical band-tension signal as a function of the compression of the compression spring 82.

Figure 16:
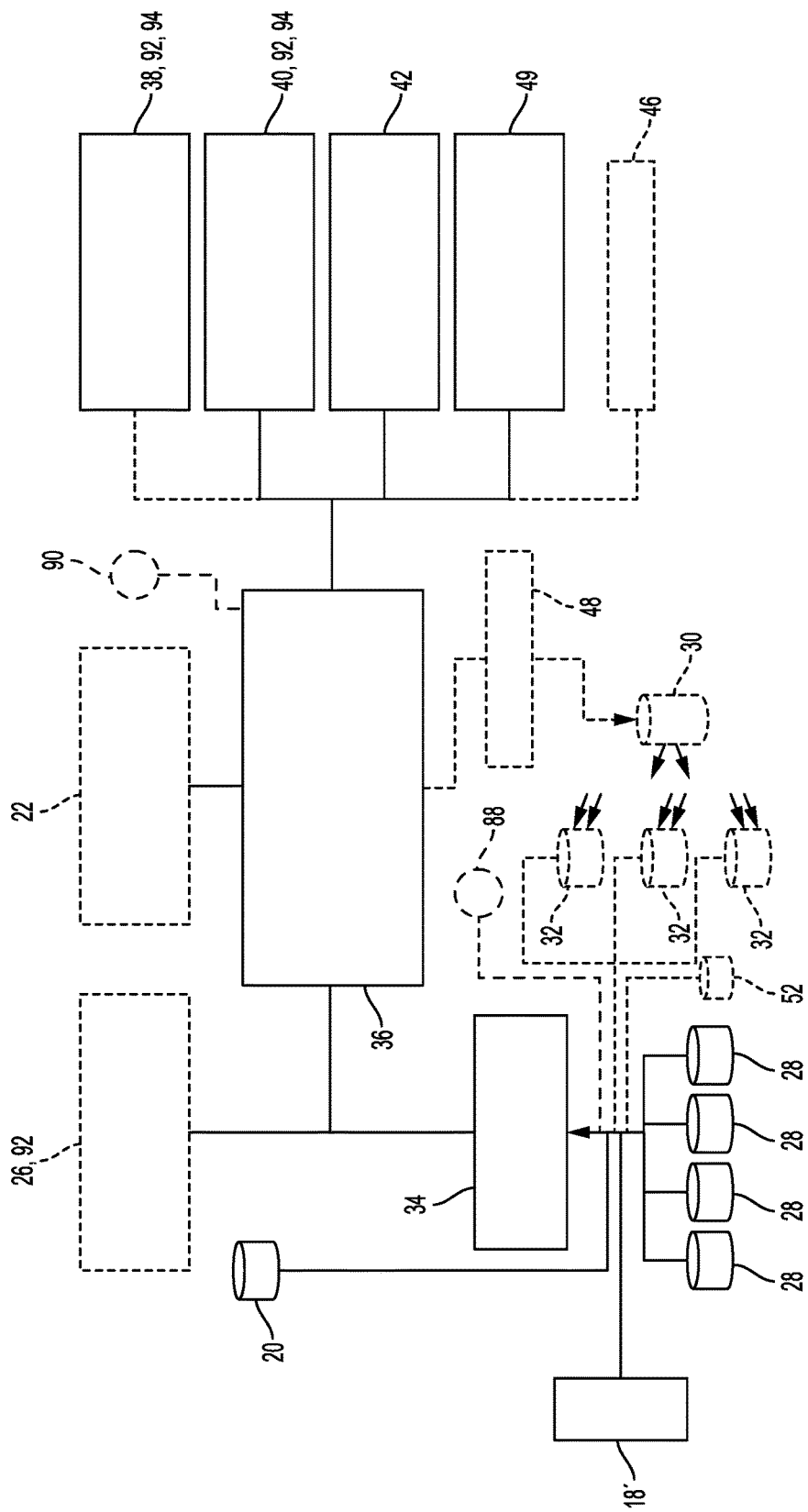
FIG. 16 shows a second diagram of the measurement arrangement and the electronic circuit thereof.

The embodiment of the electronic circuit 60 shown in FIG. 16 is very similar to that as per. FIG. 2.

The electrical pressure signals from the e.g. four pressure sensors 28, the electrical band-tension signal from the band-tension sensor 18' and the electrical air-pressure output signal from the air-pressure sensor 20 are fed to the A/D converter 34 (analog/digital converter), which supplies the appropriate converted signals to the microprocessor 36. It should be noted here that the air-pressure sensor 20 can be dispensed with if the pressure sensors 28 and, if need be, the contact-pressure sensor 52 are not designed as absolute-pressure sensors but as relative-pressure sensors. The air-pressure output signal is used in the microprocessor 36 for the air-pressure-dependent correction of the pressure signals or the contact-pressure signal in order to obtain appropriate air-pressure-independent signals for further processing. If there is a contact-pressure sensor 52 in place of the band-tension sensor 18', or in addition thereto, the contact-pressure signal from the former is also supplied to the A/D converter 34 and, therefrom, to the microprocessor 36.

Additionally, the USB interface 40, the storage device 42 and the power supply 44, preferably with a battery or a rechargeable battery, are connected to the microprocessor 36 in a well-known fashion.

There preferably are an accelerometer 46 and an RF interface 38, which are likewise connected to the microprocessor 36.

Furthermore, the transmitter of the infrared sensor 30, if present, is connected to the microprocessor 36 via the amplifier and the D/A converter 48. The possibly present detectors 32 of the infrared sensor 30 (three in the illustrated example) emit their output signals to the A/D converter 34 and, via the latter, to the microprocessor 36.

Furthermore, the input keys 26 and the display 22 are also connected to the microprocessor 36.

For completeness' sake, reference is made to the fact that there may also be a temperature sensor 88, the electrical signal of which is supplied to the microprocessor 36 via the A/D converter 34. By way of example, the temperature sensor 88 can be used to measure the temperature of the subject at the measurement location and/or the temperature in the electronic circuit 60 in order to obtain information regarding the temperature of the subject or to correct temperature-dependent signals if required or to monitor the reaching and maintaining of the operational temperatures. Furthermore, an optical or acoustic alarm transmitter 90 can be connected to the microprocessor. It goes without saying that it is feasible to integrate an optical alarm transmitter into the display 22.

The electronic circuit has an input body 92; the latter can be formed individually or in combination by the input keys 26, the RF interface 38 and the USB interface 40. The input body 92 is used for entering commands and externally established values, which will be gone into in conjunction with the description of the flowcharts in FIGS. 17, 18 and 20.

The USB interface 40 furthermore serves for the connection to an external computer for programming the microprocessor 36 and, if need be, for transmitting data registered by the apparatus to the computer for the purposes of further evaluation. The same applies to the RF interface 38.

Finally, the electronic circuit 60 also has an output body 94. It can be formed individually or in combination by the display 22, the RF interface 38 and the USB interface 40. The display 22 is used to display the measurement results, alarms, states and instructions for operation. The RF interface 38 and the USB interface 40 serve as output bodies to transmit established data and, if need be, internal data to the external computer.

Figure 17:
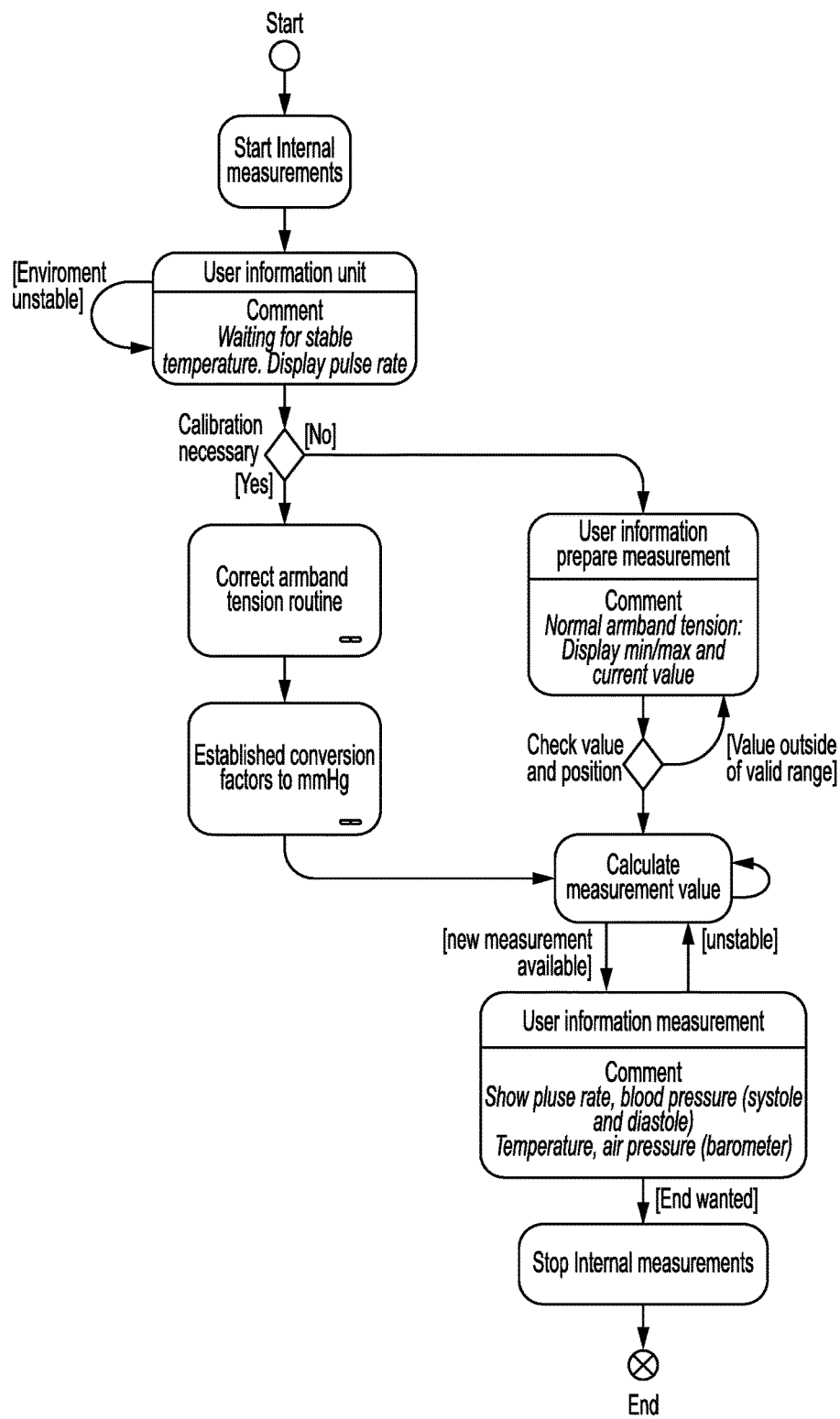
FIG. 17 shows a flowchart of an overview over the start-up steps from the start, after attaching the apparatus, up until the end.
Figure 18:
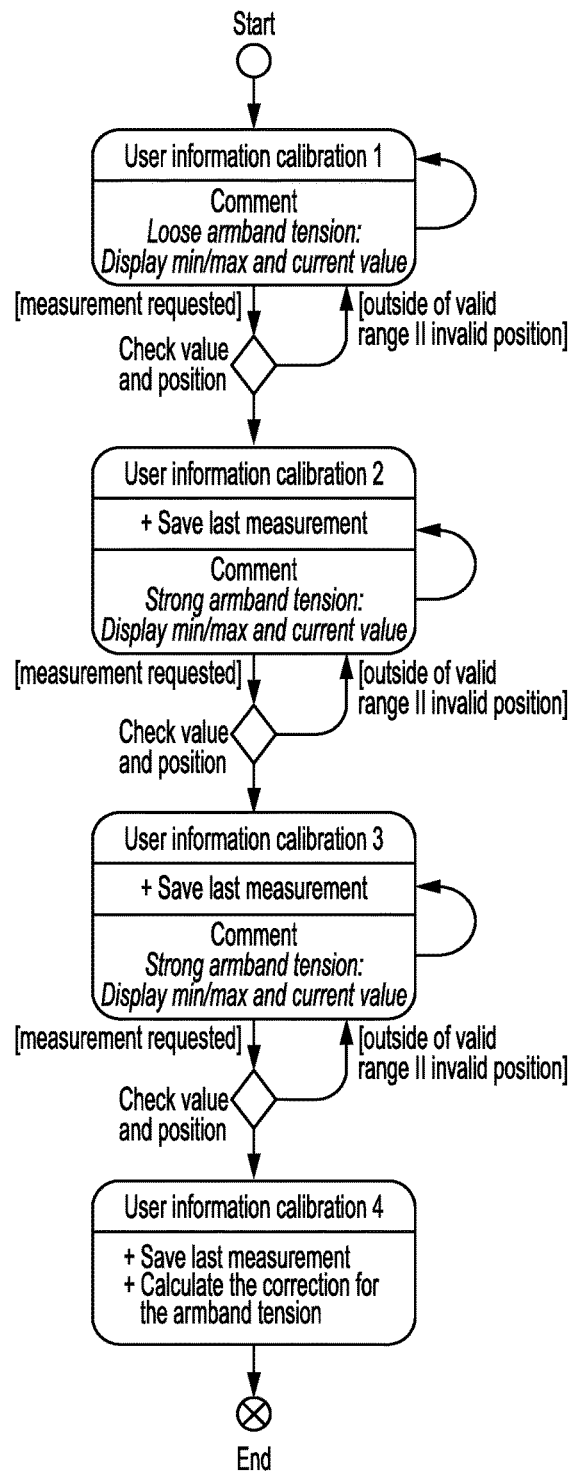
FIG. 18 shows steps of the "correct armband tension routine" in FIG. 17, likewise in the form of a flowchart.
Figure 20:
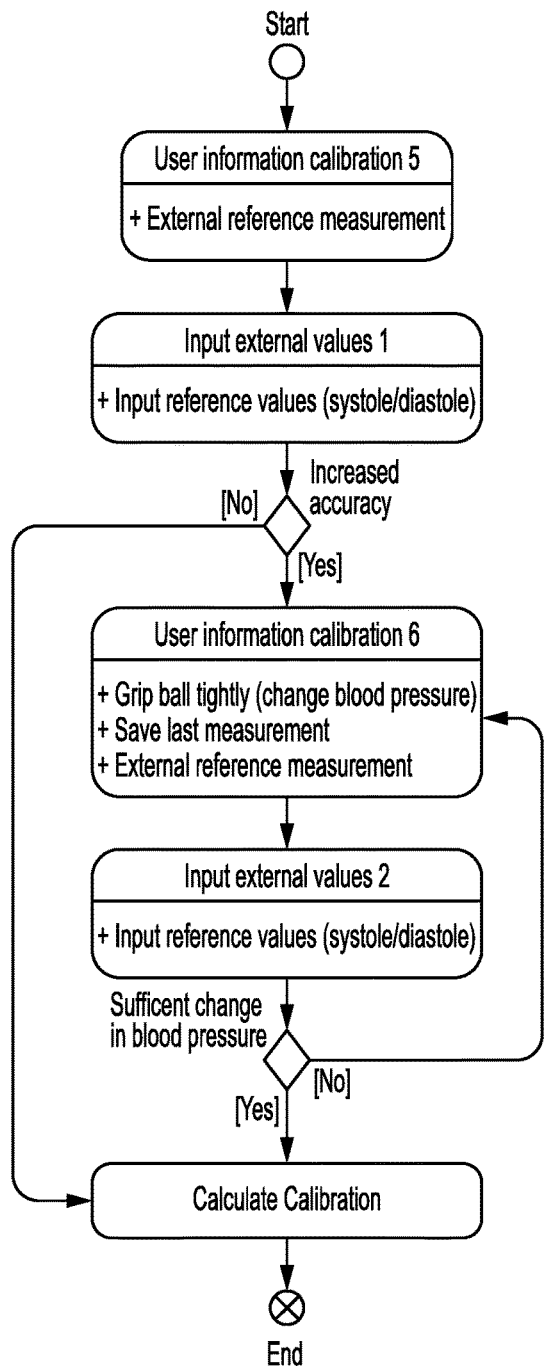
FIG. 20 shows steps of the "establish conversion factors to mmHg" routine in FIG. 17 in the form of a flowchart.

The operation and the functionality of the apparatus and the processing specific to the invention of the signals in the microprocessor 36 emerge from the flowcharts shown in FIGS. 17, 18 and 20. The flowchart in FIG. 17 provides an overview of the most important steps after attaching the apparatus to the suitable location on the skin of the body until after the desired measurements of the blood pressure have been completed.

Once the apparatus (FIG. 1 or 8) has been attached to a suitable location on an extremity and the band 14 surrounding the extremity has been tightened such that the apparatus is seated on the location in a comfortable fashion but cannot slip, the apparatus is switched on, for example by pressing the input key 26 "START". This starts internal measurements, such as stability measurements and function monitoring.

As soon as these have been completed successfully, the microprocessor 36 proceeds to a "user information init" routine that relates to initializing the user information. Herein the microprocessor 36 for example checks whether the environment is stable, more particularly if the temperature of the apparatus (in this case the internal temperature) established by the temperature sensor 88 is stable. The pressure signal from the pressure sensor or sensors 28 is already being evaluated, and the established pulse rate is displayed on the display 22, along with the comment "Waiting for stable temperature".

As soon as the microprocessor 36 determines stable conditions, a decision is made as to whether or not calibration is necessary. The apparatus itself decides in favor of calibration for example if it is used for the first time, if it has not been used for a certain, long period of time, if values, e.g. relating to correction and examination functions, are missing or are recognized as being unreliable, etc. However, this decision can, if need be, also be made by an operating person or the user (if this option is provided), for the purpose of which a corresponding question appears on the display 22. A calibration is initialized by pressing the "YES" input key 26, which is followed by a "correct armband tension routine" being run through and then an "establish conversion factors to mmHg" routine, after which the continuous measurement of the blood pressure with the calculation of the measurement values in the microprocessor 36 is started. The "correct armband tension routine" and the "establish conversion factors to mmHg" routine are discussed in more detail in conjunction with FIGS. 18-21.

However, if no calibration is required, this is confirmed by pressing the "NO" input key 26.

If no calibration is required, the apparatus runs through the "user information prepare measurement" routine. In the process, the instruction "Normal armband tension:" appears on the display; this means that there should be a normal (average) armband tension, and a predetermined minimum allowable armband tension, a predetermined maximum allowable armband tension are displayed, as well as the current value of the armband tension. The armband tension emerges from the band-tension signal from the band-tension sensor 18' or, should the latter not be present, from the contact-pressure signal from the contact-pressure sensor 52. The microprocessor 36 checks whether the value lies in a valid range between the minimum and maximum allowable value and, should this not be the case, initializes by means of the display on the display that the band 14 should be tensioned to a greater or a lesser extent. This step is repeated until the measured armband tension or the measured contact pressure lies in the valid range. As soon as this is the case, the continuous measurement of the blood pressure with the calculation of the measurement values is started.

The signals from the sensors are preferably sampled at a rate of approximately 40 Hz. This allows very precise evaluation of the measured pressure, temperature and acceleration signals.

In addition to calculating the pulse rate, the blood pressure (systole and diastole), the temperature and the air pressure, the "calculate measurement value" routine also continuously checks whether there are stable conditions. By way of example, this is brought about by checking plausibility and whether the measurement values or the changes thereof lie within predetermined limits. If unstable conditions are determined over a certain amount of time, the microprocessor 36 initializes the alarm transmitter 90 in order to make the user or the operating person aware of this.

If there are stable conditions, the respectively calculated measurement values, pulse rate, blood pressure (systole and diastole), temperature and air pressure are shown on the display 22, which is brought about in the "user information measurement" routine.

If the end of the measurement is desired, the corresponding input key 26 is actuated. This stops the internal measurements in the apparatus ("stop internal measurements").

Calculated measurement values and the correction functions can be stored in the storage device 42 if the apparatus is subsequently switched off.

It is also mentioned that the entries and the displays can be brought about on an external computer if the latter is or remains connected to the apparatus via the USB interface 40, for example.

FIG. 14 is now used to describe how the correction function for the armband tension is established by means of the "correct armband tension routine". Once this routine has started, the step "user information calibration 1" is brought about, in which the band-tension signal from the band-tension sensor 18' or the contact-pressure signal from the contact-pressure sensor 52 is evaluated. To this end, the comment "Loose armband tension" is displayed on the display 22 and a predetermined minimum allowable value and a predetermined maximum allowable value are displayed, as well as the current value. If the current value is above the maximum allowable value, the operating person or the user must loosen the band 14 by means of the catch 16 until the current value lies within the allowable range. The band 14 must accordingly be tightened if the current value lies below the minimum allowable value. The microprocessor 36 checks whether the current value lies in the valid range between the minimum value and the maximum value.

The microprocessor 36 ensures that all calibration measurements are carried out in stationary and unchanging position of the measurement location using the signals from the accelerometer 46, which is preferably a 3-axis accelerometer.

If the measured value lies within the valid range, the microprocessor 36 proceeds to the step "user information calibration 2". The last measurement of the armband tension or the contact pressure is stored at the beginning of this step, together with the pressure signals from the pressure sensors 28. Subsequently the comment "Strong armband tension!" is initialized on the display, and the corresponding predetermined minimum value and predetermined maximum value are displayed, as well as the currently measured value. The user or an operator should tighten the band 14, preferably in steps, until the checking of the value by means of the microprocessor 36, and hence the display, results in said value lying within the valid range between the maximum and the minimum value.

If the band-tension signal or the contact-pressure signal lies within the valid range, the microprocessor 36 proceeds to the step "user information calibration 3". The preceding last measurement, namely the band-tension signal or the contact-pressure signal and the simultaneously measured pressure signals from the pressure sensors 28, at a strong band tension, are stored at the beginning of this step.

Then the comment "Normal armband tension" appears on the display and appropriate predetermined maximum and minimum allowable values are displayed, as well as the currently measured value. The user or an operating person must then again reduce the tension in the band 14 by means of the catch 16 until the microprocessor 36 determines that the current value lies within a valid range, which is shown on the display 22.

If the check by means of the microprocessor 36 has yielded that the current value lies within the allowable valid range, the step "user information calibration 4" is carried out. In the process, the last measurement at normal armband tension is stored, i.e. the relevant band-tension signal or contact-pressure signal and the simultaneously measured pressure signals from the pressure sensors 28 are stored. It should be mentioned at this point that while the "correct armband tension routine" is executed, care has to be taken that the apparatus (more particularly the pressure sensors 28 and possibly the contact-pressure sensor 52) remain at the same site and position and the user acts such that their blood pressure is as constant as possible.

The values measured for the loose armband tension, the strong armband tension and the normal armband tension are used to calculate a correction function for the subsequent correction of the armband tension, as described below with the aid of FIG. 19.

Figure 19:
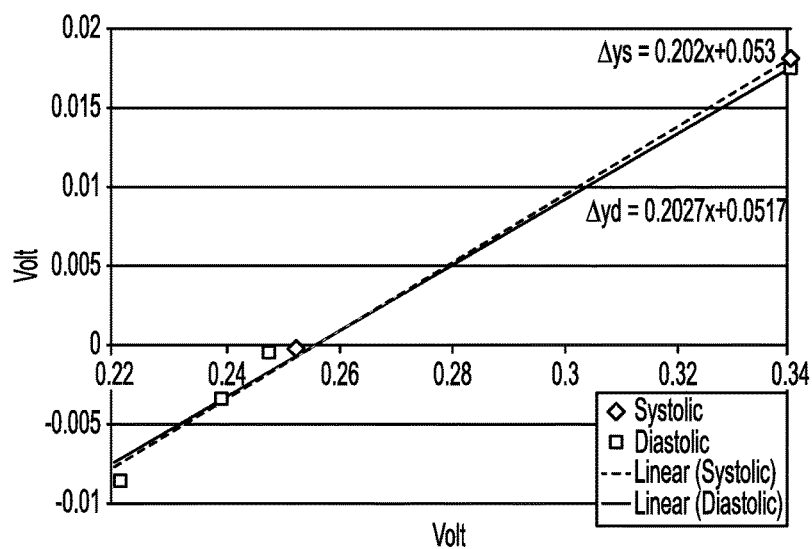
FIG. 19 shows an example of a correction function established by means of the "correct armband tension routine"

In FIG. 19, the abscissa specifies the measured voltage (in volt) of the band-tension signal or the contact-pressure signal. The ordinate relates to the measured voltage (in volt) of the zero-corrected pressure signal from the pressure sensors 28. For reasons of improved clarity, FIG. 19 only plots the values of the systole (diamond) and diastole (square), determined from the pressure signal from a single pressure sensor 28 on a test user, as a function of the band-tension signal or contact-pressure signal in the three above-described calibration steps (loose armband tension, normal armband tension and strong armband tension). These calibration measurement values can be used to establish a correction function (for each pressure sensor 28) by means of a linear regression, which correction function is illustrated in FIG. 19 (for the determined pressure sensor 28) using a full straight line for the diastole and using a dashed straight line for the systole.

A correction function $$\Delta yd = kd^*x + dd$$

is determined for the diastole by means of the linear regression and a correction function $$\Delta ys = ks^*x + ds$$

is determined for the systole, in which x specifies the band tension or the contact pressure in millivolt and the factors kd and ks specify the gradient and the factors dd and ds specify the offset and $\Delta yd$ and $\Delta ys$ specify the correction value as a function of the band tension or the contact pressure.

In the illustrated example, the correction function $\Delta ys = 0.208x + 0.053$ was calculated for the systole and the correction function $\Delta yd = 0.2027x + 0.0517$ was calculated for the diastole.

During the "calculate measurement value" routine, the respective value for the systole and the diastole arising from the pressure signal is corrected as a function of the band-tension signal or the contact-pressure signal, according to the formula:

$$yd = \text{measured value of the diastole} - \Delta yd$$

or, for the systole, $$ys = \text{measured value of the systole} - \Delta ys.$$

This compensates for the change in the band tension, for example as a result of a change in the girth of the relevant extremity as a result of exercise, change in air pressure or the like.

In order to be able to establish the effective blood-pressure values from the values for the systole and diastole, corrected by the correction functions for the armband tension, a further calibration is necessary, which is brought about in the "establish conversion factors" routine and explained in more detail with reference to FIG. 20. For completeness' sake, reference is made to the fact that the assumption is made both in this calibration step and when establishing the correction function for the armband tension that the blood pressure of the user of the apparatus remains constant during the calibration period. This can be ensured by virtue of the fact that, on the one hand, the user maintains the same comfortable position and that, on the other hand, the microprocessor carries out a plausibility check of the measured values. Otherwise the relevant calibration steps should be repeated.

After the "establish conversion factors to mmHg" routine was started, the display 22 displays "External reference measurement" in the step "user information calibration 5". This is brought about after the blood pressure was measured by means of the apparatus, for example during 5 minutes after the measurements to establish the band-tension dependence, and at least approximately constant values were established in the process. The blood pressure of the user should then be measured using a recognized measurement method, for example by means of a calibrated oscillatory blood-pressure measuring apparatus. If, for example, the apparatus has been attached on the forearm in the vicinity of the wrist, the blood pressure is preferably measured on the upper arm of the same arm by means of the oscillatory blood-pressure measuring apparatus.

Then, in the step "input external values 1", the apparatus demands by means of a corresponding display on the display 22 that the externally measured reference values for systole and diastole are entered. This entry can be brought about by means of either the input keys 26 or an external computer connected to the apparatus. It is also feasible for the external blood-pressure measuring apparatus to communicate directly with the apparatus according to the invention and to transmit the measured reference values of the systole and diastole thereto by these means.

A linear calibration function $$Pd = gd * yd + od$$

is determined for the diastole and a linear calibration function $$Ps = gs * ys + os$$

is determined for the systole from, on the one hand, the externally measured blood-pressure values (in mmHg) for the systole and the diastole by means of the recognized oscillatory blood-pressure measurement and, on the other hand, from the measurement values (in mV) from the pressure sensor 28 or pressure sensors corrected by means of the correction function Δyd and Δys.

The assumption is made that in the normal case (=no increased accuracy) a 1-point calibration suffices for the offset (od and os), while the amplification factors gd and gs represent pressure-sensor-specific fixed factors. In the illustrated embodiment, these amplification factors depend on the sensitivity of the relevant sensor element 56 (mV/mmHg) multiplied by a correction factor depending on the properties of the relevant plunger; the length, the friction conditions, the elasticity/stiffness, the damping, etc. may be relevant. It follows that the plungers 58 are designed to be as stiff as possible in order to obtain good sensitivity. In particular, if the apparatus is used for the first time, the microprocessor 36 reacts with "Yes" at the decision "increased accuracy" so that the amplification factors gd and gs are established by means of a 2-point calibration. During further usage of the apparatus, the user or the operating person can then select the type of calibration at this decision by pressing the appropriate input key "Yes" or "No" in order to increase the measurement accuracy.

If the decision is made that "increased accuracy wanted"="Yes", the so-called 2-point calibration is carried out. To this end, a further measurement is carried out at a changed, preferably higher, blood pressure in addition to the above-described external reference measurement. By way of example, to this end, the user can tightly hold a ball in their hand, as specified in the step "user information calibration 5". This increases the blood pressure and this increase is established by means of the pressure sensors 28. If this measurement is assessed to be acceptable by the microprocessor 36 according to prescribed criteria (e.g. stability, blood-pressure difference), said microprocessor stores the corresponding values for the systole and the diastole, corrected by the correction function, and, by means of an appropriate display on the display 22, demands a further external reference measurement. As described above, this is for example brought about by means of the external oscillatory blood-pressure measuring apparatus.

In the step "input external values 2", a corresponding display on the display 22 demands the entry of the externally established reference values for the systole and diastole. The entry is brought about as described above in conjunction with the step "input external value 1".

The microprocessor 36 then checks whether or not there is a sufficient change in the blood pressure. If not, there once again is a new internal and external measurement until there was a sufficient blood-pressure change. If this is the case, the microprocessor 36 calculates the linear calibration functions for the diastole and systole using the values for the systole and diastole, measured by means of the pressure sensors 28 and corrected by the correction function, and also the corresponding externally measured reference values for diastole and systole.

Figure 21:
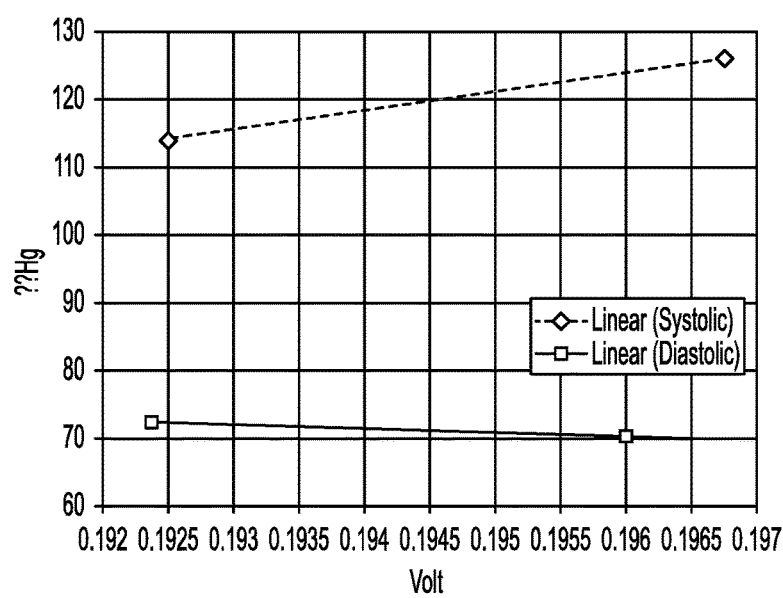
FIG. 21 shows an example of a correction function established by means of the routine as per FIG. 20.

FIG. 21 shows an example of calibration functions established in this manner. The abscissa specifies the pressure signal from a pressure sensor 28, corrected by the correction function, as a voltage in volt. The relevant externally measured reference values for the systole and diastole are plotted along the ordinate. The calibration function for the diastole is illustrated using a full straight line, and the one for the systole is illustrated using a dashed straight line.

If "increased accuracy" is not required, the microprocessor 36 then calculates the offset od for the diastole and the offset os for the systole from the blood-pressure values established by the first external reference measurement and the corresponding values for the diastole and systole, established by the pressure sensors and corrected by the correction function, wherein use is made of the previously established and stored values of the amplification factors gq and gs.

Once the calibration functions have been calculated, the continuous measurement and calculation of the blood-pressure values can commence, as was described in conjunction with FIG. 17. The microprocessor 36 activates the alarm transmitter 90 during the measurement if the blood-pressure values for the diastole or systole cross upper and lower thresholds. It is mentioned for completeness' sake that the blood-pressure values continuously established over a long period of time can be stored together with time information in the storage device 42 and this data can then be output to an external computer via one of the interfaces 38, 40 for further evaluation and for archiving purposes.

The apparatus can be built with a size of the order of a wristwatch. Since additionally no artery needs to be occluded or partly occluded for measurement purposes, the apparatus is also suitable for continuous monitoring of the blood-pressure values and pulse values in the daily routine of the user without impeding the latter.

By way of example, the microprocessor 36 can select the signal from the pressure sensor 28 signals with the best blood-pressure signals for further processing. In the case of the embodiment with pressure sensors 28 and a contact-pressure sensor 52, the microprocessor 36 can additionally also determine which one or more of these sensors 28, 52 is used as a contact-pressure sensor 28 on the basis of the corresponding signals.

The invention claimed is:

1. An apparatus for continuously measuring the blood pressure of a user for monitoring purposes, the apparatus comprising:
   a housing with a bearing plate that forms a housing base;
   at least one pressure sensor having a first plunger with a first external free end suitable for resting against a site on the external surface of the body of the user, the pressure sensor continuously measuring during calibration and continuous measurement the pressure at the site influenced by the blood pressure and generating a corresponding electrical pressure signal;
   a band suitable for encompassing the body and holding the pressure sensor against the surface at the site with safe, functional contact;
   a contact-pressure sensor having a second plunger with a second external free end, wherein the second external free end is suitable for resting against the external surface of the body of the user, continuously measuring the contact pressure during calibration and continuous measurement, and generating a corresponding electrical contact-pressure signal; and
an electronic circuit comprising a current supply, a microprocessor for establishing a diastolic and a systolic blood-pressure value, taking into account the contact-pressure signal when processing the simultaneously measured pressure signal, and an output element for displaying or outputting the blood-pressure values, wherein:
the first plunger and the second plunger both interact with an associated piezo-resistive sensor element fixedly arranged on a printed circuit board;
the first external free end of the first plunger of the pressure sensor protrudes relative to and by a first distance beyond the bearing plate; and
the second external free end of the second plunger of the contact-pressure sensor protrudes relative to and by a second distance beyond the bearing plate, wherein the first fixed distance is greater than the second fixed distance.

2. The apparatus as claimed in claim 1, wherein the microprocessor is suitable for establishing a correction function as a function of the corresponding contact-pressure signal and the pressure signal depending on the band tightened to a different extent during a number of calibration steps, in order to correct the pressure signal as a function of the contact-pressure signal during the continuous measurement.

3. The apparatus as claimed in claim 2, wherein the correction function is established by linear regression and the band is tightened in a step-like fashion during the number of calibration steps.

4. The apparatus as claimed in claim 1, wherein the band is provided with a catch in order to be able to tighten the band to a greater and lesser extent during the number of calibration steps.

5. The apparatus as claimed in claim 4, wherein the catch is a stepped catch.

6. The apparatus as claimed in claim 1, wherein the pressure sensor protrudes no more than 1 mm with respect to the bearing plate.

7. The apparatus as claimed in claim 1, wherein the smaller amount by which the contact-pressure sensor protrudes beyond the bearing plate is approximately half the amount by which the pressure sensor protrudes.

8. The apparatus as claimed in claim 1, further comprising an input element for entering at least one externally measured diastolic and systolic effective blood-pressure value, wherein the microprocessor is suitable for establishing a calibration function from these effective blood-pressure values and the pressure signal, which was corrected by the correction function if need be, in order to establish the effective blood-pressure values during the continuous measurement.

9. The apparatus as claimed in claim 1, further comprising an air-pressure sensor, the electrical air-pressure output signal of which is fed to the microprocessor.

10. The apparatus as claimed in claim 9, wherein the electrical air-pressure output signal is fed to the microprocessor for correcting the pressure signal and, if need be, for correcting the contact-pressure signal.

11. The apparatus as claimed in claim 9, wherein the pressure sensor is embodied as an absolute-pressure sensor and the contact-pressure sensor is likewise embodied as an absolute-pressure sensor.

12. The apparatus as claimed in claim 1, further comprising an accelerometer, the electrical acceleration output signal of which is fed to the microprocessor for evaluation.

13. The apparatus as claimed in claim 1, further comprising a temperature sensor, the electrical temperature output signal of which is fed to the microprocessor for evaluation.

14. The apparatus as claimed in claim 1, further comprising an infrared transmitter with an associated detector, the electrical detector output signal of which is fed to the microprocessor for evaluation.

15. The apparatus as claimed in claim 1, wherein the electronic circuit has an acoustic or optical alarm transmitter, which can be actuated by the microprocessor in order to trigger an alarm if prescribable alarm thresholds for the diastolic and systolic blood pressure are exceeded or undershot.

16. A method for continuously measuring the blood pressure of a user for monitoring purposes, in which:
at least one pressure sensor is brought to rest against a site on the external surface of the body of the user;
the pressure influenced by the blood pressure is continuously measured at the site by means of the pressure sensor during calibration and continuous measurement and a corresponding electrical pressure signal is generated, wherein the pressure sensor has a first plunger with a first external free end;
the body is encompassed by a band for holding the pressure sensor against the surface at the site with safe, functional contact;
a contact pressure is continuously measured by means of a contact-pressure sensor during calibration and continuous measurement, wherein the contact-pressure sensor has a second plunger with a second external free end, wherein the first plunger of the pressure sensor protrudes relative to and by a first distance beyond a bearing plate and the second plunger of contact-pressure sensor protrudes relative to and by a second distance beyond the bearing plate, wherein the first distance is greater than the second distance, and wherein the first and the second plungers both interact with an associated piezo-resistive sensor element fixedly arranged on a printed circuit board;
a corresponding electrical contact-pressure signal is generated; and
a diastolic and a systolic blood-pressure value is established from the pressure signal via a microprocessor of an electronic circuit with a current supply, taking into account the contact-pressure signal when processing the simultaneously measured pressure signal, and said blood-pressure value can be displayed or output by means of an output element.

17. The method as claimed in claim 16, wherein the band is tightened to a different extent during a number of calibration steps and a correction function is established as a function of the corresponding contact-pressure signal and the pressure signal via the microprocessor in order to correct the pressure signal by the correction function, as a function of the contact-pressure signal, during the continuous measurement.

18. The method as claimed in claim 17, wherein the correction function is established by linear regression and the band is tightened in a step-like fashion during the number of calibration steps.

19. The method as claimed in claim 17, wherein an externally measured diastolic and systolic effective blood-pressure value is entered and the microprocessor establishes a calibration function from these effective blood-pressure values and the pressure signal, which if need be was corrected by the correction function, in order to establish the effective diastolic and systolic blood-pressure value during the continuous measurement.

* * * * *